United States Patent
Zalman et al.

(10) Patent No.: US 11,155,510 B2
(45) Date of Patent: Oct. 26, 2021

(54) HYDROFORMYLATION SYSTEM WITH VENT REACTOR RECYCLE TO PRIMARY REACTOR

(71) Applicant: OQ Chemicals Corporation, Houston, TX (US)

(72) Inventors: Kyle J. Zalman, Needville, TX (US); Markus Heuwes, Bay City, TX (US); Christopher J. Bischoff, Bay City, TX (US)

(73) Assignee: OQ Chemicals Corporation, Houston, TX (US)

( * ) Notice: Subject to any disclaimer, the term of this patent is extended or adjusted under 35 U.S.C. 154(b) by 0 days.

(21) Appl. No.: 16/920,856

(22) Filed: Jul. 6, 2020

(65) Prior Publication Data

US 2021/0040023 A1    Feb. 11, 2021

Related U.S. Application Data

(60) Provisional application No. 62/884,727, filed on Aug. 9, 2019.

(51) Int. Cl.
| | | |
|---|---|---|
| *C07C 45/50* | (2006.01) | |
| *C07C 45/78* | (2006.01) | |
| *B01J 4/00* | (2006.01) | |
| *B01J 19/00* | (2006.01) | |
| *B01J 19/18* | (2006.01) | |
| *B01J 31/18* | (2006.01) | |

(52) U.S. Cl.
CPC ............... *C07C 45/50* (2013.01); *B01J 4/001* (2013.01); *B01J 19/0053* (2013.01); *B01J 19/18* (2013.01); *B01J 31/1845* (2013.01); *C07C 45/78* (2013.01); *B01J 2531/822* (2013.01)

(58) Field of Classification Search
CPC ................................ C07C 45/50; C07C 45/78
See application file for complete search history.

(56) References Cited

U.S. PATENT DOCUMENTS

| | | |
|---|---|---|
| 4,151,209 A | 4/1979 | Paul et al. |
| 4,593,127 A | 6/1986 | Bunning et al. |
| 5,105,018 A | 4/1992 | Miyazawa et al. |
| 5,367,106 A | 11/1994 | Unruh et al. |
| 9,067,876 B2 | 6/2015 | Becker et al. |
| 9,688,598 B2 | 6/2017 | Eisenschmid et al. |
| 9,695,098 B2 | 7/2017 | Miller et al. |

OTHER PUBLICATIONS

International Search Report and Written Opinion in corresponding PCT patent application dated Oct. 2, 2020.

*Primary Examiner* — Sikarl A Witherspoon
(74) *Attorney, Agent, or Firm* — Michael Ferrell

(57) ABSTRACT

A hydroformylation system for making aldehydes includes: (a) a primary reactor provided with catalyst feed, syngas feed and olefin feed adapted to convert the olefin and syngas to product aldehyde; (b) a first liquid vapor separator coupled to the primary reactor for receiving output therefrom, adapted to separate the product aldehyde into a crude aldehyde product stream and a vent stream containing syngas and unreacted olefin; (c) a vent reactor coupled to the first liquid vapor separator to receive the vent stream therefrom, the vent reactor also being coupled to the primary reactor which is configured to provide catalyst thereto, wherein the vent reactor is operative to convert unreacted olefin in the vent stream from the first liquid vapor separator to additional product aldehyde. A second liquid vapor separator is coupled to the vent reactor to receive output therefrom and adapted to separate the output from the vent reactor into a liquid recycle stream containing additional product aldehyde and catalyst as well as another vent stream, the second liquid vapor separator also being coupled to the primary reactor so as to provide the recycle stream thereto.

22 Claims, 3 Drawing Sheets

HYDROFORMYLATION SYSTEM WITH VENT REACTOR RECYCLE TO PRIMARY REACTOR

CLAIM FOR PRIORITY

This application is based on U.S. Provisional Application No. 62/884,727 of the same title, filed Aug. 9, 2019. The priority of U.S. Provisional Application No. 62/884,727 is hereby claimed and its disclosure incorporated herein by reference.

TECHNICAL FIELD

The present invention relates to hydroformylation of olefins to make aldehydes utilizing a vent reactor with catalyst and product recycle to a primary reactor from a liquid vapor separator associated with the vent reactor.

BACKGROUND

Processes for hydroformylating an olefin to prepare a carbonyl derivate containing one carbon atom more than the starting olefin by reacting the olefin with carbon monoxide and hydrogen, which mixture is also known as synthesis gas (syngas), in the presence of a Group VIII metal, e.g., rhodium, in complex combination with an organic ligand and carbon monoxide are well known in the art (referred to as "OXO" processes) and have enormous industrial importance:

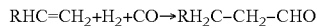
$$RHC=CH_2+H_2+CO \rightarrow RH_2C-CH_2-CHO$$

wherein R is an organic radical. Commercial olefin feedstocks which may be utilized are ethylene, propylene, and 1- and 2-butenes, pentenes, hexenes and the like. In general, any suitable olefin having a C2 (ethylene) to C6 (hexene) carbon content may be used. A single methyl branch at the olefinic carbon of a terminal olefin reduces its reaction rate by a factor of ten, but the effect of a branch diminishes as its distance from the double bond increases. Some C6 feedstocks which exhibit different reactivities include: 1-hexene; 4-methyl-1-pentene; 2-hexene; 4-methyl-2-pentene; 2-methyl-1-pentene; 2-methyl-2-pentene; and 2,3-dimethyl-2-butene.

U.S. Pat. No. 5,367,106 to Unruh et al. (1994) discloses an OXO process with a coupled vent reactor for making aldehydes. U.S. Pat. No. 9,695,098 to Miller et al. discloses a hydroformylation system utilizing a vent reactor with product recycle from the vent reactor to a common product/catalyst separator. See, also, U.S. Pat. No. 5,105,018 to Miyazawa et al., U.S. Pat. No. 9,067,876 to Becker et al., U.S. Pat. No. 4,593,127 to Bunning et al., as well as U.S. Pat. No. 9,688,598 to Eisenschmid et al.

Because substantial amounts of the unreacted components are in the various streams, it is important to operate the systems in ways that maximize product recovery and minimize waste of raw material. Capital and energy operating costs are likewise important to efficient operation and there is an ongoing need in the art for improvements which reduce capital and operating costs.

SUMMARY OF INVENTION

The present invention is directed to an improvement in a hydroformylation system for making aldehydes from olefins and syngas having a primary reactor and a vent reactor receiving unreacted olefin and syngas from the primary reactor and generating additional product aldehydes. The improvement includes a liquid vapor separator receiving the output from the vent reactor and returning a liquid stream comprising catalyst and additional product aldehyde from the vent reactor to the primary reactor.

Details are provided in the description following and in the appended Figures.

It will be appreciated from the discussion which follows that advantages of the invention include lower capital and energy operating costs since a flasher, flasher pre-heater and a receiver vessel suitable for the flasher can be eliminated. Moreover, olefin gas loss points through vents are reduced, reducing raw material costs and reducing waste emissions. With the inventive system the catalyst life is extended since the catalyst remains under pressure with syngas and reactant olefin, reducing deactivation and precipitation of the catalyst complex.

BRIEF DESCRIPTION OF DRAWINGS

The present invention is described in connection with the Figures in which.

DETAILED DESCRIPTION

Figure 1:
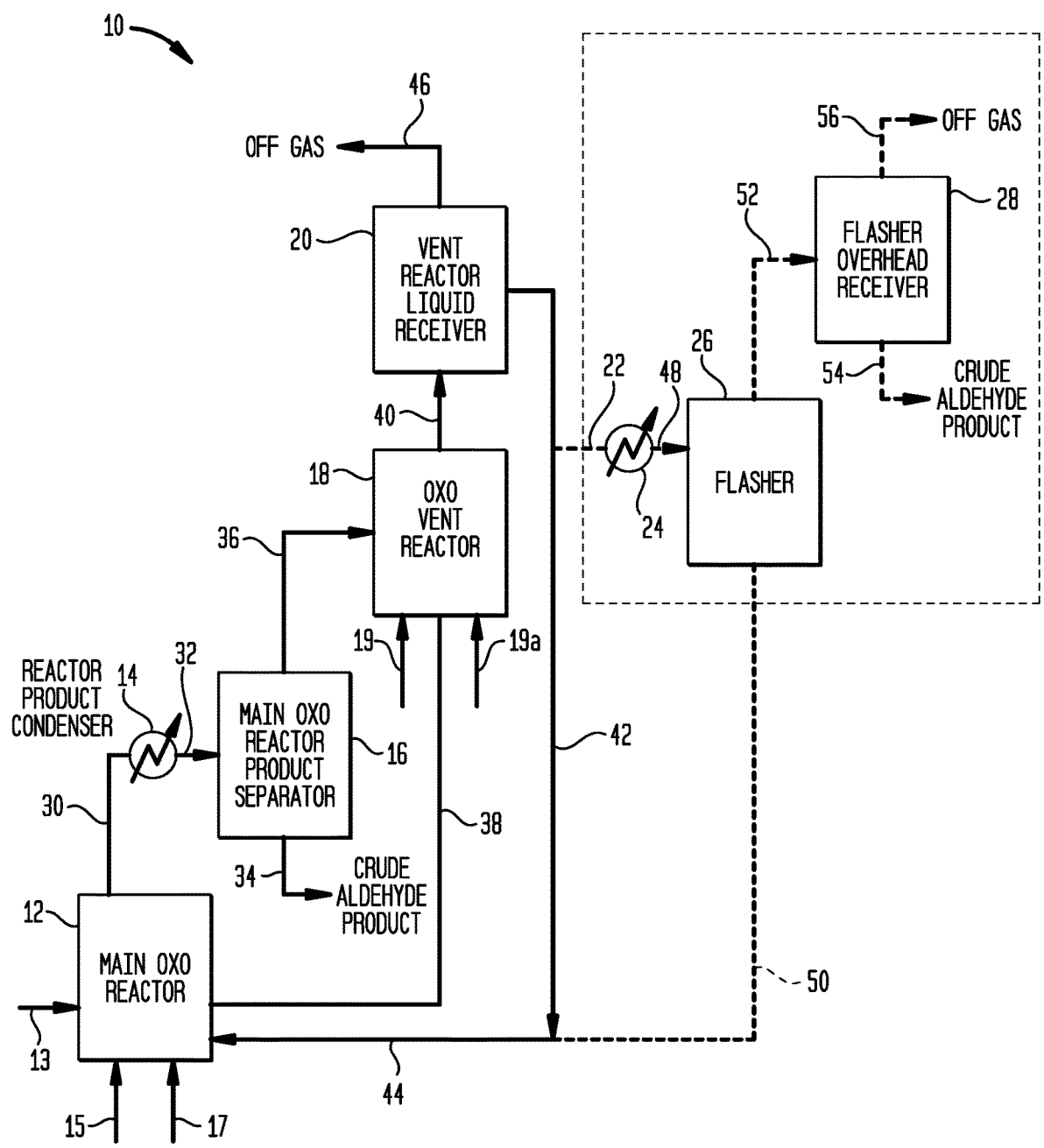
FIG. 1 is a schematic diagram illustrating an embodiment of the system of the invention with liquid recycle from a vent reactor to a primary reactor through a liquid receiver.

It is to be understood that the particular hydroformylation reaction conditions employed in either the primary reactor or the vent reactor or the secondary reaction process are not critical to the subject invention and may be varied widely and tailored to meet the individual needs of the particular reactors utilized as well as to produce the particular aldehyde product desired.

Group VIII catalyst metals include rhodium, ruthenium, palladium, osmium, iridium, and combinations thereof, particularly, rhodium and ruthenium and especially rhodium, are employed in organometallic complexes as catalysts for the reaction of syngas with olefins to form aldehyde derivatives of the olefins which have one more carbon atom than the parent olefin. A wide range of olefinic feedstocks can be employed, including substituted olefins. While the present invention is broadly applicable to the hydroformylation of olefins of 2-20 carbon atoms, its most useful application are especially with alpha-olefins of 2 to 8 carbon atoms. The system and process is particularly suitable for hydroformylating ethylene and propylene to propionaldehyde and n-butyraldehyde respectively. In this invention, the same catalyst complex and olefin are used for both the primary reactor and vent reactor. The catalyst is circulated continuously between the two reactors and the unconverted olefin in the primary reaction process is introduced into the vent reactor which may be a plug-flow or back mixed reactor for conversion of the unreacted olefin to aldehyde.

The hydroformylation processes are typically carried out at superatmospheric pressure, typically under a partial pressure of about 4 to 20 atmospheres of hydrogen and carbon monoxide combined and with the molar ratio of hydrogen to carbon monoxide being in the range of about 0.5:1 to 10:1.

The hydroformylation reaction temperature in the reactors is usually within range of 80° C. to 170° C., preferably in the range from about 120° C. to about 140° C.

The liquid reaction medium or catalyst solution which is employed comprises, (a) the catalyst complex, (b) typically, an excess of the organic ligand employed in forming the complex over and above the mount required to complex the metallic component of the catalyst, (c) the hydroformylation reaction product along with by-products typically resulting from undesired condensation of the hydroformylation product aldehyde with itself, (d) a quantity of the olefin being hydroformylated, in an amount varying with the molecular weight of said olefin (the proportion of liquid olefin in the reaction medium usually being greater with high molecular weight olefins than with lower alkanes such as ethylene), and (e) optionally an inert reaction solvent.

The catalytic metal is complexed with hydrogen and carbon monoxide as well as with an organic ligand. While many organic ligands can be employed, those of particular significance comprise either monodentate or polydentate triorganophosphines, triorganophophites, triorganoarsines, or triorganostibines, with the phosphines and phosphites being of particular industrial importance. Simple monodentate phosphines and phosphites, as exemplified by triphenylphosphine and triphenylphosphite, are commonly employed industrially. However, polydentate ligands have advantages in that the large excesses of ligand which are often used with the monodentate ligands are not needed. The catalytic complex can be formed in situ in the hydroformylation reactor, or it can be preformed.

The concentration of catalyst to be maintained in the hydroformylation reaction medium is not critical to the successful employment of the present invention. Typically, however, when the catalytic metal is rhodium and when the ligand is triphenylphosphine, the liquid reaction medium will contain about 0.01 to 1.0% rhodium and up to about 20% or more triphenylphosphine by weight where suppression of iso-aldehydes is desired. In hydroformylating ethylene, the iso-aldehydes problem does not exist, and low ligand concentrations can be employed. In the absence of the added inert reaction solvent, the triphenylphosphine content in hydroformylating propylene, for example, may be as high as about 40%.

Inert solvent, which is optionally used in the reaction system, is not overly critical so long as it be miscible with the catalyst system and with the reactants and reaction products, low in volatility so as to facilitate stripping reaction product and by-products from it, and, of course, either chemically inert in the hydroformylation reaction system or else forming in that system a derivative which is, itself, inert while still fulfilling the other named requirements. (That is, a suitable solvent could be one which might undergo hydrogenation in the reactor and then in the hydrogenated form, be inert to further reaction.) Molecular weight is not a significant factor in the reaction solvents except as it relates to volatility, relatively high molecular weight being desired, of course, to facilitate retention of the inert solvent as a heavy end while the reaction products are stripped. It is already known to employ any of a large number of inert liquids including, for example, alkyl-substituted benzenes; pyridine and alkyl-substituted pyridines; tertiary amines; high-boiling esters such as dialkyldicarboxylates and triorganophosphates, as well as esters of polyols such as trimethylolpropane and pentaerythritol; ketones; alcohols such as the butanols; nitriles such as acetonitriles; and hydrocarbons including both saturated hydrocarbons such as kerosene, mineral oil, cyclohexane, naphtha, etc. and aromatics such as biphenyl. It is taught in U.S. Pat. No. 4,151,209 that particularly useful solvents include triphenylphosphine oxide and polyglycols, e.g., polyethylene glycol and polypropylene glycol, which have molecular weights of at least about 500.

Referring to FIG. 1, there is shown a hydroformylation system 10, including a primary OXO reactor 12, a condenser 14, a main OXO reactor product separator 16, a vent reactor 18 and a vent reactor liquid receiver 20.

Also shown in FIG. 1 are components in a conventional system surrounded by a dashed line border which can be eliminated by way of the present invention. Conventional components include a feed line 22, a flasher pre-heater 24, a flasher 26, as well as a flasher overhead receiver 28.

In operation, flow of the various streams is in the direction indicated by the arrows in FIG. 1. Primary OXO reactor 12 is fed with catalyst, syngas and olefin reactant at 13, 15 and 17 which are reacted to provide an aldehyde containing vaporous product stream which exits reactor 12 through line 30 and is provided to a condenser 14 where the product is cooled and provided to separator 16 through line 32. In separator 16, the liquid is withdrawn from the system as crude product at 34 and a vapor vent stream is provided to vent reactor 18 through line 36.

Optionally, reactor 18 is provided with additional syngas and reactant olefin, as may be required for optimal operation, as indicated by arrows 19, 19a.

Vent reactor 18 is coupled to reactor 12 via line 38 which provides a catalyst from the primary reactor to vent reactor 18. That is, a portion of the liquid catalyst solution containing the rhodium-complex catalyst, any free organophosphorus ligand, solvent, a small amount of product aldehyde and any liquid heavy end product is continuously withdrawn from the primary OXO reactor. The withdrawn portion of the liquid catalyst solution is directed to the vent reactor which may be a plug-flow or back mixed reactor where it is mixed with the non-condensed vent gas separated from the product taken overhead from separator 16. Additional syngas is typically added to the vent gas prior to mixing with the liquid catalyst solution in the vent reactor.

In vent reactor 18, reactant olefin from main OXO separator 16 is converted to additional aldehyde product. The output from reactor 18, preferably the entire output, including vapor, dissolved gasses, solvent and heavy ends circulating in the system are provided to receiver 20 via line 40 with or without additional cooling. The liquid from receiver 20, including catalyst, crude aldehyde product, dissolved gasses, solvent and heavy ends circulating in the system, is recycled to primary reactor 12 by way of lines 42, 44. Offgas is vented at 46. The product aldehyde from the vent reactor may thus be recovered from the main separator 16.

The system of the invention differs from conventional operation of a hydroformylation system which typically contains the items shown in dashed lines and/or within the dashed lines shown in FIG. 1. In particular, conventional practice involves providing liquid output from receiver 20 to a flasher preheater 24 through line 22 (line 42 not being present in a conventional system). Preheater 24 feeds flasher 26 through line 48, where the product aldehyde is flashed off and the remaining liquid, including catalyst and any solvents, and heavies circulating in the system are returned to reactor 12 via lines 44, 50. Flashed vapor from flasher 26 is provided to flasher overhead receiver 28 via line 52 where crude aldehyde product is drawn off through line 54 and vent gasses removed at 56.

In the embodiment illustrated in FIG. 1, the product separators or receivers may be simply knock-out drums with or without cooling preceding the separator or receiver. Cooling may be provided by way of a separate condenser, such as condenser 14 or may be integral with the separator or receiver.

Figure 2A:
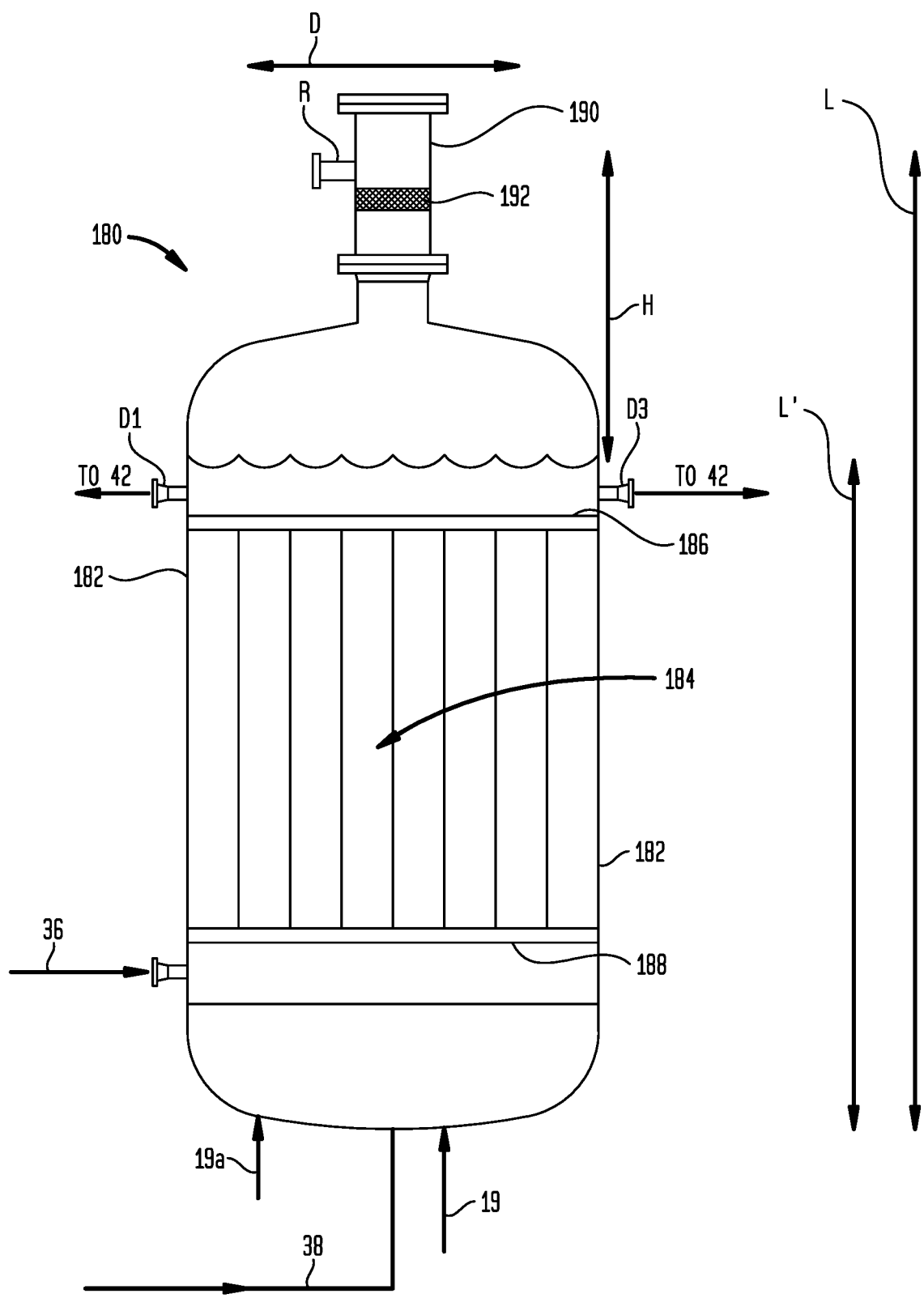
FIG. 2A is a schematic view in elevation and section of an integrated vent reactor/liquid vapor separator incorporated into the system of FIG. 1.
Figure 2B:
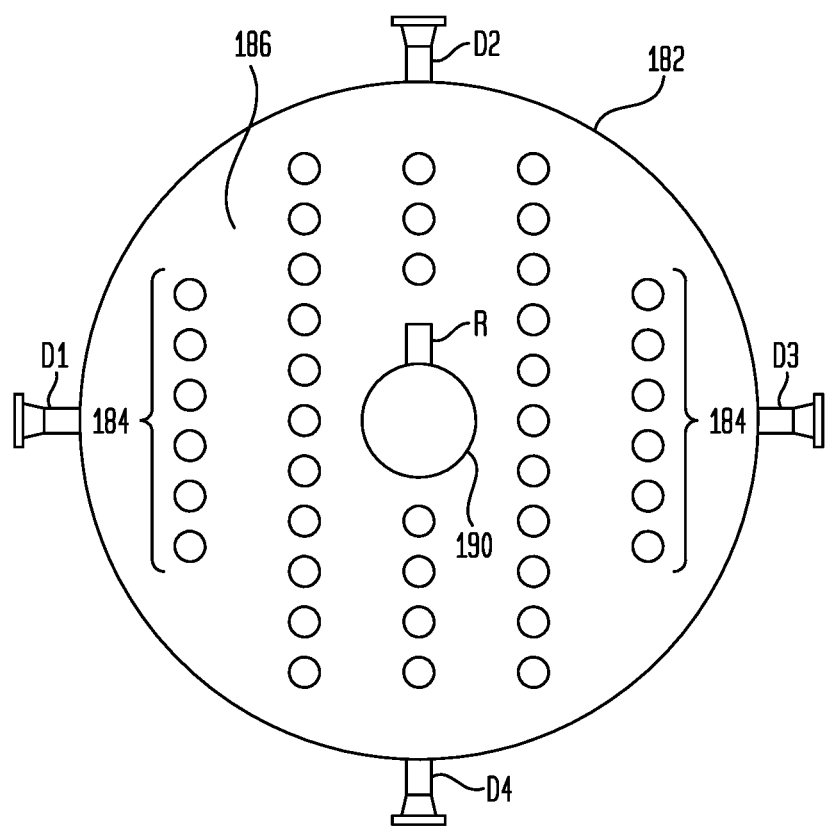
FIG. 2B is a schematic plan view in section of the integrated vent reactor/liquid vapor separator of FIG. 2A.

One preferred embodiment of the invention includes an integrated vent reactor/liquid vapor separator as is shown in FIGS. 2A and 2B which is incorporated into system 10 of FIG. 1. In FIG. 2A there is shown schematically in elevation and section an integrated vent reactor/liquid vapor separator 180 used in the system of FIG. 1 instead of vent reactor 18 and separate liquid receiver 20. Vent reactor/liquid vapor separator 180 includes a shell 182 with a plurality of tubes indicated at 184, an upper tube sheet 186, a lower tube sheet 188, a plurality of liquid exit nozzles, D1, D2, D3 and D4. Also provided is a vent gas exit manifold 190 with a vent gas exit nozzle R, and a mist eliminator 192. Vent reactor/liquid vapor separator 180 is essentially a tube in shell heat exchanger type reactor (tube side reactor) with a vapor disengaging space at the top.

FIG. 2B is a plan view of vent reactor/liquid vapor separator, in section, just above upper tube sheet 186 showing liquid exit nozzles D1, D2, D3 and D4 which are equally spaced around the periphery of shell 182.

Vent reactor/liquid vapor separator 180 has a length to diameter ratio (L/D) in the range of from about 2 to 4, preferably around 3 and defines a liquid disengaging height, H, above a liquid level in the reactor such that the ratio of H/L is from about 0.1 to about 0.4, preferably around 0.2.

Vent reactor/liquid vapor separator 180 is used in system 10 of FIG. 1, coupled to the main OXO reactor 12 by way of line 38 to receive the liquid catalyst solution and coupled to separator 16 via line 36 to receive the vent stream. Optionally, vent reactor/liquid vapor separator 180 receives additional syngas and reactant olefin as indicate by arrows 19, 19a.

When operating vent reactor/liquid vapor separator 180 reacts the unreacted vent gas received via line 36 in tubes 184 of the reactor, while maintaining a liquid level L' which is slightly above nozzles D1, D2, D3 and D4. Vent gas is withdrawn via nozzle R after passing through mist eliminator 192. Vent reactor/liquid vapor separator 180 is operated under substantially the same conditions as reactor 12; that is, at temperatures of from 80° C. to 170° C., preferably from 120° C. to 140° C. and at combined partial pressures of carbon monoxide and hydrogen of from 4 atmospheres to 20 atmospheres such that recycling to the main reactor is facilitated. When we refer to "substantially the same temperature" and/or "substantially the same pressure", such reference includes within 10% of the average value of the parameters within the recited apparatus components or as part of the recited process steps where pressure is on an absolute basis and temperature is on a Celsius scale.

Liquid is withdrawn from vent reactor/liquid vapor separator 180 via nozzles D1-D4, including catalyst, crude aldehyde product, dissolved gasses, solvent and heavy ends circulating in the system is recycled to primary reactor 12 by way of lines 42, 44. The product aldehyde from the vent reactor/liquid vapor separator 180 may thus be recovered from main separator 16.

Exemplary and Preferred Embodiments

In a first aspect of the invention there is provided as Embodiment No. 1 a hydroformylation system for making aldehydes including: (a) a primary reactor provided with catalyst feed, syngas feed and olefin feed adapted to convert the olefin and syngas to product aldehyde; (b) a first liquid vapor separator coupled to the primary reactor for receiving output therefrom, adapted to separate the product aldehyde into a crude aldehyde product stream and a vent stream containing syngas and unreacted olefin; (c) a vent reactor coupled to the first liquid vapor separator to receive the vent stream therefrom, the vent reactor also being coupled to the primary reactor which is configured to provide catalyst thereto, wherein the vent reactor is operative to convert unreacted olefin in the vent stream from the first liquid vapor separator to additional product aldehyde; (d) a second liquid vapor separator coupled to the vent reactor to receive output therefrom and adapted to separate the output from the vent reactor into a liquid recycle stream containing additional product aldehyde and catalyst as well as another vent stream, the second liquid vapor separator also being coupled to the primary reactor so as to provide the recycle stream thereto; whereby catalyst from the second liquid vapor separator is recycled to the primary reactor and additional product aldehyde from the second liquid vapor separator is provided to the primary reactor and is recovered in the crude aldehyde product stream from the first liquid vapor separator.

The system of Embodiment No. 1 may include any or all of the features of Embodiments 2 through 15 listed immediately below.

Embodiment No. 2 is the hydroformylation system for making aldehydes according to Embodiment No. 1, wherein the entire output from the vent reactor is provided to the second liquid vapor separator.

Embodiment No. 3 is the hydroformylation system for making aldehydes according to Embodiment Nos. 1 or 2, wherein the system has a single crude aldehyde product outlet.

Embodiment No. 4 is the hydroformylation system for making aldehydes according to any of the foregoing Embodiments, wherein the vent stream from the first liquid vapor separator comprises product aldehyde, syngas, and unreacted olefin.

Embodiment No. 5 is the hydroformylation system for making aldehydes according to any of the foregoing Embodiments, wherein additional syngas is provided to the vent reactor.

Embodiment No. 6 is the hydroformylation system for making aldehydes according to any of the foregoing Embodiments, further comprising a condenser coupled to the primary reactor and the first liquid vapor separator.

Embodiment No. 7 is the hydroformylation system for making aldehydes according to any of Embodiment Nos. 1 to 6, wherein the second liquid vapor separator is provided with cooling.

Embodiment No. 8 is the hydroformylation system for making aldehydes according to any of Embodiment Nos. 1 to 6, wherein the second liquid vapor separator has no cooling associated therewith.

Embodiment No. 9 is the hydroformylation system for making aldehydes according to any of the foregoing Embodiments, wherein the vent reactor is a plug flow reactor.

Embodiment No. 10 is the hydroformylation system for making aldehydes according to any of Embodiment Nos. 1 to 8, wherein the vent reactor is a back mixed reactor.

Embodiment No. 11 is the hydroformylation system for making aldehydes according to any of Embodiment Nos. 1 to 10, wherein the second vapor liquid separator is integrated with the vent reactor within a common shell.

Embodiment No. 12 is the hydroformylation system for making aldehydes according to Embodiment No. 11, wherein the primary reactor, the vent reactor and the second liquid vapor separator are operated at substantially the same temperature and substantially at the same pressure.

Embodiment No. 13 is the hydroformylation system for making aldehydes according to any of the foregoing Embodiments, wherein the olefin feed comprises propylene and the aldehyde product comprises butyraldehyde.

Embodiment No. 14 is the hydroformylation system for making aldehydes according to any of the foregoing Embodiments, wherein the catalyst is a Group VIII metal complexed with a phosphorous containing ligand and carbon monoxide.

Embodiment No. 15 is the hydroformylation system for making aldehydes according to Embodiment No. 14, wherein the Group VIII metal is rhodium.

In another aspect of the invention there is provided as Embodiment No. 16 an improvement in a hydroformylation system for making aldehydes from olefins and syngas having a primary reactor and a vent reactor receiving unreacted olefin and syngas from the primary reactor and generating additional product aldehydes, wherein the improvement comprises a liquid vapor separator receiving the output from the vent reactor and returning a liquid stream comprising catalyst and additional product aldehyde from the vent reactor to the primary reactor. The improvement of Embodiment No. 16 may include any or all of the features of Embodiments 1 to 15.

In still yet another aspect of the invention, there is provided as Embodiment No. 17 a method of making aldehydes from olefins and syngas by way of hydroformylation including the steps of: (a) feeding catalyst, syngas and olefin to a primary reactor; (b) converting the syngas and olefin to a product aldehyde in the primary reactor; (c) providing the product aldehyde and unreacted syngas and unreacted olefin from the primary reactor to a first liquid vapor separator; (d) separating the product aldehyde and unreacted olefin into a liquid crude aldehyde product stream and a vaporous vent stream containing unreacted syngas and olefin; (e) feeding the vaporous vent stream from the first liquid vapor separator and catalyst from the primary reactor to a vent reactor; (f) converting unreacted olefin and syngas from the vaporous vent stream received from the first liquid vapor separator to additional product aldehyde in the vent reactor; (g) feeding output from the vent reactor to a second liquid vapor separator; (h) separating output from the vent reactor into a liquid stream containing additional product aldehyde and catalyst and an offgas stream; (i) returning the liquid stream containing additional product aldehyde and catalyst from the second liquid vapor separator to the primary reactor, whereby catalyst from the second liquid vapor separator is recycled to the primary reactor and additional product aldehyde from the second liquid vapor separator is provided to the primary reactor and is recovered in the crude aldehyde product stream from the first liquid vapor separator.

Embodiment No. 18 is the method of making aldehydes from olefins and syngas by way of hydroformylation according to Embodiment No. 17, wherein the entire output from the vent reactor is provided to the second liquid vapor separator.

Embodiment No. 19 is the method of making aldehydes from olefins and syngas by way of hydroformylation according to Embodiment Nos. 17 or 18, wherein product aldehydes are provided to a single crude aldehyde product outlet.

Embodiment No. 20 is the method of making aldehydes from olefins and syngas by way of hydroformylation according to any of Embodiment Nos. 17, 18 or 19, further comprising providing additional syngas to the vent reactor.

Embodiment No. 21 is the method of making aldehydes from olefins and syngas by way of hydroformylation according to any of Embodiment Nos. 17, 18, 19 or 20, further comprising cooling the unreacted syngas, product aldehyde and unreacted olefin in a condenser coupled to the primary reactor and the first liquid vapor separator.

Embodiment No. 22 is the method of making aldehydes from olefins and syngas by way of hydroformylation according to any of Embodiment Nos. 17, 18, 19, 20 or 21, further comprising cooling the output from the vent reactor.

Embodiment No. 23 is the method of making aldehydes from olefins and syngas by way of hydroformylation according to any of Embodiment Nos. 17, 18, 19, 20 or 21, wherein the output from the vent reactor is separated into a liquid stream containing additional product aldehyde and catalyst and an offgas stream without cooling.

Embodiment No. 24 is the method of making aldehydes from olefins and syngas by way of hydroformylation according to any of Embodiment Nos. 17 to 23, wherein hydroformylation is carried out in the primary and vent reactors while maintaining a temperature of from about 120° C. to about 140° C. in the reactors.

Embodiment No. 25 is the method of making aldehydes from olefins and syngas by way of hydroformylation according to Embodiment No. 24, wherein hydroformylation is carried out in the primary and vent reactors while maintaining a temperature of from about 122.5° C. to about 137.5° C. in the reactors.

Embodiment No. 26 is the method of making aldehydes from olefins and syngas according to any of Embodiment Nos. 17 to 25, wherein the primary reactor, the vent reactor and the second liquid vapor separator are operated at substantially the same temperature pressure and substantially the same pressure.

It is appreciated from the foregoing that advantages of the invention include lower capital costs since the flasher, flasher pre-heater and a receiver vessel can be eliminated. Moreover, olefin gas loss points through vents are reduced, reducing operating costs. Moreover, with the inventive system the catalyst life is extended since the catalyst remains under pressure with syngas and reactant olefin, reducing deactivation and precipitation of the catalyst complex.

While the invention has been described in detail, modifications within the spirit and scope of the invention will be readily apparent to those of skill in the art. Such modifications are also to be considered as part of the present invention. In view of the foregoing discussion, relevant knowledge in the art and references discussed above in connection with the Background of the Invention and detailed description, the disclosures of which are all incorporated herein by reference, further description is deemed unnecessary. In addition, it should be understood from the foregoing discussion that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A hydroformylation system for making aldehydes comprising:
    (a) a primary reactor provided with catalyst feed, syngas feed and olefin feed adapted to convert the olefin and syngas to product aldehyde;
    (b) a first liquid vapor separator coupled to the primary reactor for receiving output therefrom, adapted to separate the product aldehyde into a crude aldehyde product stream and a vent stream containing syngas and unreacted olefin;

(c) a vent reactor coupled to the first liquid vapor separator to receive the vent stream therefrom, the vent reactor also being coupled to the primary reactor which is configured to provide catalyst thereto, wherein the vent reactor is operative to convert unreacted olefin in the vent stream from the first liquid vapor separator to additional product aldehyde;

(d) a second liquid vapor separator coupled to the vent reactor so as to receive the entire output from the vent reactor and adapted to separate the output from the vent reactor into a liquid recycle stream containing additional product aldehyde and catalyst as well as another vent stream, the second liquid vapor separator also being coupled to the primary reactor so as to provide the recycle stream thereto;

whereby catalyst from the second liquid vapor separator is recycled to the primary reactor and additional product aldehyde from the second liquid vapor separator is provided to the primary reactor and is recovered in the crude aldehyde product stream from the first liquid vapor separator.

2. The hydroformylation system for making aldehydes according to claim 1, wherein the hydroformylation system consists of: (a) the primary reactor; (b) the first liquid vapor separator; (c) the vent reactor and (d) the second liquid vapor separator.

3. The hydroformylation system for making aldehydes according to claim 1, wherein the system has a single crude aldehyde product outlet.

4. The hydroformylation system for making aldehydes according to claim 1, wherein the vent stream from the first liquid vapor separator comprises product aldehyde, syngas, and unreacted olefin.

5. The hydroformylation system for making aldehydes according to claim 1, further comprising a condenser coupled to the primary reactor and the first liquid vapor separator.

6. The hydroformylation system for making aldehydes according to claim 1, wherein the vent reactor is a plug flow reactor.

7. The hydroformylation system for making aldehydes according to claim 1, wherein the vent reactor is a back mixed reactor.

8. The hydroformylation system for making aldehydes according to claim 1, wherein the second vapor liquid separator is integrated with the vent reactor within a common shell.

9. The hydroformylation system for making aldehydes according to claim 8, wherein the primary reactor, the vent reactor and the second liquid vapor separator are operated at substantially the same temperature and substantially at the same pressure.

10. The hydroformylation system for making aldehydes according to claim 1, wherein the olefin feed comprises propylene and the aldehyde product comprises butyraldehyde.

11. The hydroformylation system for making aldehydes according to claim 1, wherein the catalyst is a Group VIII metal complexed with a phosphorous containing ligand and carbon monoxide.

12. The hydroformylation system for making aldehydes according to claim 11, wherein the Group VIII metal is rhodium.

13. In a hydroformylation system for making aldehydes from olefins and syngas having a primary reactor and a vent reactor receiving unreacted olefin and syngas from the primary reactor and generating additional product aldehydes, the improvement comprising providing the entire output from the vent reactor to a liquid vapor separator which is adapted to separate the vent reactor output into a liquid stream and an offgas stream and which returns the liquid stream which includes comprising catalyst and additional product aldehyde from the vent reactor to the primary reactor.

14. A method of making aldehydes from olefins and syngas by way of hydroformylation comprising:

(a) feeding catalyst, syngas and olefin to a primary reactor;

(b) converting the syngas and olefin to a product aldehyde in the primary reactor;

(c) providing the product aldehyde and unreacted syngas and unreacted olefin from the primary reactor to a first liquid vapor separator;

(d) separating the product aldehyde and unreacted olefin into a liquid crude aldehyde product stream and a vaporous vent stream containing unreacted syngas and olefin;

(e) feeding the vaporous vent stream from the first liquid vapor separator and catalyst from the primary reactor to a vent reactor;

(f) converting unreacted olefin and syngas from the vaporous vent stream received from the first liquid vapor separator to additional product aldehyde in the vent reactor;

(g) feeding the entire output from the vent reactor to a second liquid vapor separator;

(h) separating output from the vent reactor into a liquid stream containing additional product aldehyde and catalyst and an offgas stream;

(i) returning the liquid stream containing additional product aldehyde and catalyst from the second liquid vapor separator to the primary reactor, whereby catalyst from the second liquid vapor separator is recycled to the primary reactor and additional product aldehyde from the second liquid vapor separator is provided to the primary reactor and is recovered in the crude aldehyde product stream from the first liquid vapor separator.

15. The method of making aldehydes from olefins and syngas by way of hydroformylation according to claim 14, further comprising providing additional syngas to the vent reactor.

16. The method of making aldehydes from olefins and syngas by way of hydroformylation according to claim 14, further comprising cooling the unreacted syngas, product aldehyde and unreacted olefin in a condenser coupled to the primary reactor and the first liquid vapor separator.

17. The method of making aldehydes from olefins and syngas by way of hydroformylation according to claim 14, further comprising cooling the output from the vent reactor.

18. The method of making aldehydes from olefins and syngas by way of hydroformylation according to claim 14, wherein the output from the vent reactor is separated into a liquid stream containing additional product aldehyde and catalyst and an offgas stream without cooling.

19. The method of making aldehydes from olefins and syngas by way of hydroformylation according to claim 14, wherein hydroformylation is carried out in the primary and vent reactors while maintaining a temperature of from about 120° C. to about 140° C. in the reactors.

20. The method of making aldehydes from olefins and syngas by way of hydromylation according to claim 19, wherein hydroformylation is carried out in the primary and vent reactors while maintaining a temperature of from about 122.5° C. to about 137.5° C. in the reactors.

21. The hydroformylation system for making aldehydes according to claim 1, wherein the system has a single crude aldehyde product outlet and the second liquid vapor separator is adapted to separate the vent reactor output into the liquid recycle stream and an offgas stream and which returns the entire liquid recycle stream which includes catalyst and additional product aldehyde from the vent reactor to the primary reactor.

22. The method of making aldehydes from olefins and syngas by way of hydromylation according to claim 14, wherein the second liquid vapor separator is adapted to separate the vent reactor output into a liquid stream containing additional product aldehyde and catalyst and an offgas stream and which returns the entire liquid output stream from the second liquid vapor separator which includes catalyst and additional product aldehyde from the vent reactor to the primary reactor.

\* \* \* \* \*